US009238098B2

(12) United States Patent
Bocklet et al.

(10) Patent No.: US 9,238,098 B2
(45) Date of Patent: Jan. 19, 2016

(54) METHOD OF INITIALISING AN APPARATUS FOR BLOOD TREATMENT IN THE SINGLE-NEEDLE MODE AND APPARATUS FOR BLOOD TREATMENT IN THE SINGLE-NEEDLE MODE

(75) Inventors: Christoph Bocklet, Bad Bocklet (DE); Ingo Schaefer, Eschborn (DE); Martin Thys, Grettstadt (DE); Joachim Noack, Bad Neustadt (DE); Ralf Mueller, Bad Homburg (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 395 days.

(21) Appl. No.: 13/700,586

(22) PCT Filed: Jun. 3, 2011

(86) PCT No.: PCT/EP2011/002736
§ 371 (c)(1),
(2), (4) Date: Nov. 28, 2012

(87) PCT Pub. No.: WO2011/151075
PCT Pub. Date: Dec. 8, 2011

(65) Prior Publication Data
US 2013/0079698 A1  Mar. 28, 2013

(30) Foreign Application Priority Data
Jun. 4, 2010  (DE) .......................... 10 2010 022 776

(51) Int. Cl.
*A61M 37/00* (2006.01)
*A61M 5/00* (2006.01)
*A61M 1/30* (2006.01)

(52) U.S. Cl.
CPC . *A61M 5/00* (2013.01); *A61M 1/30* (2013.01); *A61M 1/306* (2014.02); *A61M 2205/07* (2013.01)

(58) Field of Classification Search
CPC ......... A61M 5/00; A61M 1/30; A61M 1/306; A61M 2205/07
USPC ................................. 604/4.01–6.16
See application file for complete search history.

(56) References Cited

U.S. PATENT DOCUMENTS 5,141,490 A * 8/1992 Fujii et al. .................... 604/6.05

FOREIGN PATENT DOCUMENTS

| DE | 10 2005 001779 A1 | 9/2006 |
| DE | 10 2007 026009 A1 | 1/2009 |
| EP | 0 405 094 A2 | 1/1991 |
| EP | 0 472 480 A1 | 2/1992 |
| GB | 2 141 936 A | 1/1985 |
| WO | 2008/148505 A1 | 12/2008 |

OTHER PUBLICATIONS

International Search Report from PCT/EP2011/002736 mailed on Oct. 19, 2011.
International Preliminary Report on Patentability from PCT/EP2011/002736 mailed on Dec. 13, 2012.

* cited by examiner

*Primary Examiner* — Philip R Wiest
(74) *Attorney, Agent, or Firm* — Kenyon & Kenyon LLP (57) ABSTRACT

An apparatus and method for blood treatment for the single-needle mode, the apparatus having an extra-corporeal blood circuit with a blood infeed line running to the inlet and a blood return line leading away from the outlet, of a blood treating unit, includes in the blood return line a device, e.g., container, for amassing blood, which is in flow-permitting connection for gas transfer with a device, e.g., container, for storing gas. A pressure is calculated and set in the device for storing gas before the arterial and venous phases are started, with two constraints. First, the pressure should be sufficiently low to ensure both no infusion of air into the patient and also regulated flow of blood into the patient even at opposing pressures lower than ambient pressure. Second, the pressure should be sufficiently high to expel blood from the device for amassing blood into the device for storing gas.

20 Claims, 3 Drawing Sheets

METHOD OF INITIALISING AN APPARATUS FOR BLOOD TREATMENT IN THE SINGLE-NEEDLE MODE AND APPARATUS FOR BLOOD TREATMENT IN THE SINGLE-NEEDLE MODE

CROSS REFERENCE TO RELATED APPLICATIONS

The present application claims priority International Patent Application No. PCT/EP2011/002736, filed on Jun. 3, 2011, which claims priority to Application No. DE 10 2010 022 776.5, filed in the Federal Republic of Germany on Jun. 4, 2010.

FIELD OF INVENTION

The present invention relates to a method of initialising an apparatus for blood treatment for the single-needle mode, which apparatus has an extra-corporeal blood circuit which has a blood infeed line running to the inlet of a blood-treating unit and a blood return line leading away from the outlet of the blood-treating unit, with the blood infeed line and blood return line respectively leading away from and running to one common needle (catheter). As well as this, the present invention also relates to an apparatus for blood treatment in the single-needle mode.

BACKGROUND INFORMATION

Types of blood-treatment apparatus having a blood-treating unit through which the blood of a patient flows are generally familiar. They include for example the known types of apparatus for haemodialysis, haemofiltration and haemodiafiltration. The known types of blood-treatment apparatus can be operated in the single-needle or double-needle mode.

In the double-needle mode, the blood is withdrawn from a blood vessel of the patient via a first needle, is conveyed to the blood-treating unit of the blood-treatment apparatus and is fed back into a blood vessel of the patient via a second needle. Replaceable tubing sets having a blood infeed line and a blood return line to which the two needles are connected are used for the withdrawal and return of the blood. These tubing sets, which are thrown away after use, are also referred to as disposables.

In the single-needle mode, the withdrawal and return of the blood take place via a single needle. During an arterial phase, the blood withdrawn from the patient is stored in a reservoir, before being then fed back from the reservoir to the patient's circulation through the same needle in a venous phase.

A blood-treatment apparatus for the single-needle mode is described in German Application No. DE 10 2007 026 009. This known blood-treatment apparatus has an extra-corporeal blood circuit which has a blood infeed line running to the inlet of a blood-treating unit and a blood return line leading away from the outlet of the blood-treating unit. This extra-corporeal blood circuit having the blood-treating unit need not be part of the blood-treatment apparatus but may be a disposable intended for once-only use which is inserted in the treating unit for the purpose of the blood treatment.

As well as this, the blood-treatment apparatus also has a device for amassing blood and a device for storing gas and in particular air. The devices for amassing blood and for storing gas are each a reservoir which creates a sealed-off volume of space, and are for example respective blood and air chambers of a preset volume.

The device for amassing blood is connected to the device for storing gas, thus enabling air which is expelled from the device for amassing blood to make its way into the device for storing gas in the venous phase when the device for amassing blood is being filled, and air to make its way from the device for storing gas into the device for amassing blood in the venous phase whereby the blood which previously amassed in the arterial phase is expelled from the device for amassing blood. What is achieved in this way is that blood is withdrawn from the patient in the arterial phase and the blood which has been treated by the blood-treating unit is fed back again to the patient in the venous phase.

The connection between the device for amassing blood and the device for storing gas has a first and a second connecting path. The first connecting path connects the device for amassing blood and the device for storing gas in such a way that air expelled from the device for amassing blood is transferred to the device for storing gas in the arterial phase, with a device for interrupting the connection being provided in the first connecting path. The second connecting path connects the device for amassing blood and the device for storing gas in such a way that air which was stored in the device for storing gas is transferred to the device for amassing blood in the venous phase. The second connecting path includes a device for compressing gas, thus enabling the air which was stored in the device for storing gas to be transferred to the device for amassing blood. A preset pressure can be generated in the device for amassing blood by the device for compressing the air both during the arterial phase and during the venous phase. The device for compressing gas may for example take the form of a conventional compressor.

Together with the first and second connecting paths, the device for amassing blood and the device for storing gas form sealed-off volumes of space which no gas is able to enter and from which no gas is able to escape. Only for the purposes of initialisation is air admitted to/released from the sealed-off volume of space.

For trouble-free and safe operation of the blood-treatment apparatus in the single-needle mode, it must be ensured that air is not under any circumstances able to be infused into the patient.

In the known blood-treatment apparatus, the possibility of blood being infused into the patient is intended to be ruled out by setting, in the device for storing gas, a pressure which under no circumstances in operation is higher than the pressure which arises in the device for amassing blood. What is intended to be achieved by this device is that air is only able to make its way from the device for storing gas into the device for amassing blood with the help of the device for compressing gas. If on the other hand there is a failure of the device for compressing gas, such as a leak in the compressor for example, no air is to be able to make its way into the device for amassing blood. This is intended to rule out the possibility of the device for amassing blood unintentionally running dry, as a result of which air might make its way into the patient.

In the known blood-treatment apparatus, an initialisation of the system takes place before the arterial and venous phases are started. To enable the condition to be met that, when there is a low return pressure and a high cardiac output, air is not to be able to make its way from the device for storing gas into the device for amassing blood if there is a failure of the compressor, the system is depressurised to a preset pressure, which is preferably ambient pressure, to initialise the successive arterial and venous phases, at the time of the changeover from the arterial to the venous phase, i.e., at the time of the upper changeover point at which the device for amassing blood is full. In the successive arterial and venous phases, the pressure in the device for storing gas is thus always below the preset pressure, and particularly ambient pressure, to which the sealed-off system has been de-pressurised.

It is found to be a disadvantage that, before the arterial and venous phases are started, the device for amassing blood has to be filled with blood until the filled level has reached the upper changeover point. What is more, it is necessary for a given blood level in the device for amassing blood to be set beforehand.

SUMMARY

An object underlying the present invention is to increase the safety of blood treatment in the single-needle mode and/or to simplify the initialisation of the successive arterial and venous phases.

The method and apparatus according to the present invention are based on the calculation of a pressure which is set in the device for storing gas before the arterial and venous phases are started. This maximum pressure is of a size such that air cannot under any circumstances make its way into the patient. In calculating the pressure, there are two constraints which are taken into account. On the one hand, the pressure should be sufficiently low to ensure both that any possibility of an infusion of air into the patient is ruled out and also that there is still an assurance of the flow of blood into the patient being regulated even at opposing pressures which are lower than ambient pressure. On the other hand, the pressure should be sufficiently high for it to be possible for a mass of air to be made available which is sufficiently large to expel the blood from the device for amassing blood into the device for storing gas.

Because the pressure to be set in the device for storing gas is calculated in the method and apparatus according to the present invention, it is not necessary for the pressures in the device for amassing blood and the device for storing gas at the lowest and highest filled levels to be measured. As well as this, the initialisation to start the arterial and venous phases can be started at any time regardless of the level of the liquid at the time. It is not necessary for the liquid level at the lowest and highest filled levels to be set nor are any devices required for determining the level of the liquid.

The pressure (below atmospheric) previously calculated can easily be set before the arterial and venous phases are started by discharging gas from the device for storing gas, preferably into the atmosphere. However, in particular cases, such for example as when there is a particularly high opposing venous pressure, when the patients are in particular positions, or at particular geodetic altitudes, it may also be sensible for a pressure above atmospheric to be set in the device for storing gas. To set a pressure above atmospheric, gas is fed into the device for amassing blood.

To calculate the pressure to be set in the device for storing gas, the volume of gas contained in the device for amassing blood is preferably determined and the pressure to be set in the device for storing gas is then determined on the basis of this volume of gas contained in the device for amassing blood. Rather than the volume of gas contained in the device for storing gas, it is also possible for the volume of blood contained in the device for amassing blood to be determined to enable the pressure to be set to be calculated on the basis of this volume of blood contained in the device for amassing blood. Because the volume of space enclosed in the device for amassing blood is known, the volume of gas can be calculated from the volume of blood, or vice versa, as the case may be.

To determine the volume of gas contained in the device for amassing blood, a preset difference in pressure is preferably produced between the device for amassing blood and the device for storing gas. Basically, this difference in pressure may be of any desired level. For this purpose, gas is transferred from the device for storing gas to the device for amassing blood, the absolute pressure in the device for storing gas and the absolute pressure in the device for amassing blood being determined before and after the production of the difference in pressure. It is immaterial in this case how the pressure in the device for storing gas and the absolute pressure in the device for amassing blood are determined. The pressure may for example be measured with respective pressure sensors which are arranged inside the volumes of space enclosed by the device for storing gas and the device for amassing blood. Basically however it is equally possible for the pressures to be measured in the lines which are connected to the device for amassing blood and the device for storing gas when the pressures in the chambers and lines have equalised. To determine the absolute pressures in the device for storing gas and the device for amassing blood, absolute pressures or relative pressures may be measured.

When it is relative pressures which are being measured, a preferred exemplary embodiment makes provision for ambient pressure to be measured for the purpose of determining the absolute pressures. The respective relative pressures are measured in the device for storing gas and the device for amassing blood. The value of the absolute pressure is then calculated from the values of the relative pressure and of ambient pressure. This has the advantage that sensors of relative pressure which, though they generally have a smaller range of measurement than sensors of absolute pressure, are more accurate within this smaller range of measurement, can be used to measure the pressures in the chambers. What is more, sensors of relative pressure are available at low cost.

Before gas is transferred from the device for storing gas into the device for amassing blood, a pressure which corresponds to ambient pressure is set in the sealed-off volume of space in the device for amassing blood and in the sealed-off volume of space in the device for storing gas. This gives a defined initial state for the production of the difference in pressure. It is however also possible for the pressure in the device for amassing blood to be increased from a pressure other than ambient pressure in order to produce a difference in pressure.

To set the ambient pressure, a connection is preferably made between the device for storing gas and the device for amassing blood and air is admitted to/released from the device for storing gas and/or the device for amassing blood. Suitable devices for air admission/release are provided for the admission/release of the air. Because both the devices are in flow-permitting connection, it is enough for the admission/release of air to take place on only one side of the system as a whole.

In a preferred exemplary embodiment of blood-treatment apparatus according to the invention, the device for making a connection between the device for amassing blood and the device for storing gas have two connecting paths. One connecting path comprises a line for feeding gas which connects the device for storing gas to the device for amassing blood. The device for compressing gas, which is a compressor for example, is arranged in this line. The other connecting path comprises a bypass line which bypasses the device for compressing gas and in which a bypass valve is arranged. When the device for compressing gas is not being operated, the bypass valve is closed and the sealed-off volume of space in the device for amassing blood is isolated from the sealed-off volume of space in the device for storing gas. When on the other hand the bypass valve is open, the two volumes of space form one common sealed-off volume of space. However, for the determination of the pressure to be set in the device for amassing blood, it is immaterial how the device for amassing blood and the device for storing gas communicate with one another. It is also immaterial how gas is transferred from the device for amassing blood to the device for storing gas and vice versa. All that is crucial is that a sealed-off volume of space is available which air is admitted to/released from only to start the initialisation.

The device for amassing blood preferably takes the form of a container of a preset volume which has an inlet and an outlet and which is arranged in the blood return line of the extra-corporeal circuit. The device for storing gas also preferably takes the form of a container of a preset volume.

The device for amassing blood are preferably an integral part of a disposable cassette, and in particular are an integral single-needle chamber in a disposable blood cassette for haemodialysis such as is described in German Patent Application No. DE 10 2009 024 468 and International Patent Application No. PCT/EP2010/002488. At least parts of the blood lines which run to and lead from the device for amassing blood are preferably an integral part of the blood cassette.

The containers may be bags made of a flexible material. The containers are preferably film bags which are intended for once-only use (disposables). However, when the containers take the form of disposables, there must be a suitable receiving unit in which the film bags can be inserted and which ensures that the bags will withstand negative and positive opposing pressures without, in the respective cases, collapsing or expanding.

The blood in the extra-corporal circuit is preferably fed by a blood pump which is arranged in the blood infeed line.

Exemplary embodiments of the present invention will be explained in detail below with reference to the accompanying drawings.

DETAILED DESCRIPTION

Figure 1:
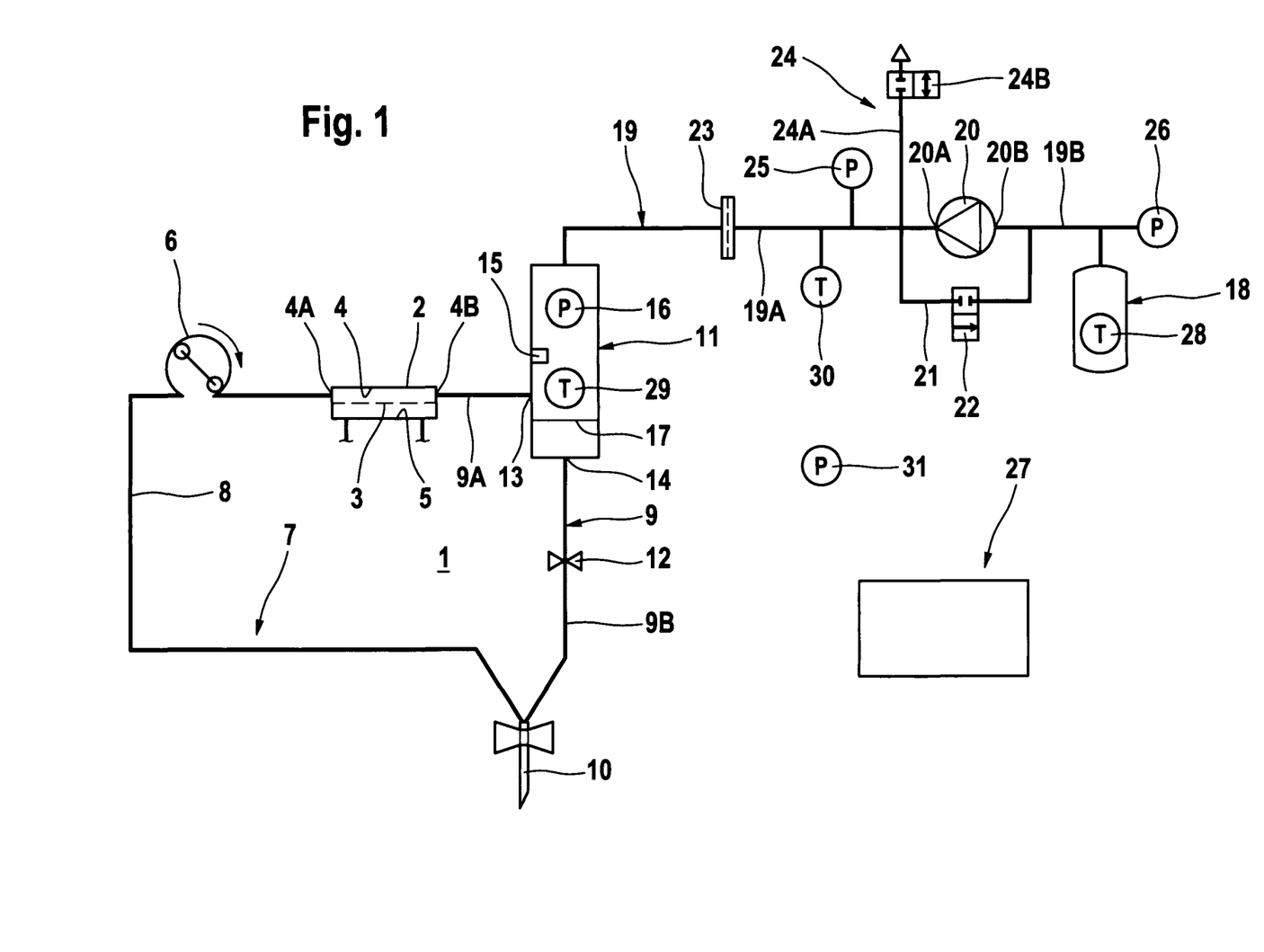
FIG. 1 is a highly simplified schematic view of an exemplary embodiment of blood-treatment apparatus according to the present invention for the single-needle mode.

FIG. 1 is a schematic view showing the main components of a blood-treatment apparatus, and in particular a dialysis apparatus for the single-needle mode which, except for the initialisation according to the present invention to start the arterial and venous phases, is described in German Application No. DE 10 2007 026 009.

The dialysis apparatus has, during the blood treatment, an extra-corporeal blood circuit 1 which comprises a blood-treating unit 2, such as a dialyser for example, in the form of a disposable. The dialyser 2 is divided into a blood chamber 4 and a dialysis-fluid chamber 5 by a semi-permeable membrane 3.

The blood is fed in the extra-corporeal blood circuit by means of a blood pump 6 which is part of the dialysis apparatus. The circuit for the dialysis fluid is not shown in FIG. 1.

There is inserted into the dialysis apparatus a tubing set 7 which is discarded after the treatment. This disposable 7 has a blood infeed line 8 which runs to the inlet 4A of the blood chamber 4 of the dialyser and which is inserted in the roller pump 6 of the dialysis apparatus, and a blood return line 9 which leads away from the outlet 4B of the blood chamber. The blood infeed and return lines 8, 9 are connected to a common needle (catheter) 10.

Arranged in the blood return line 9 of the disposable there is a device 11 for amassing blood which takes the form of a container of a preset volume. The device for amassing blood will be referred to in what follows as a blood reservoir 11.

Downstream of the blood reservoir 11, a device 12 for closing off the blood return line 9, such as a venous tube clamp for example, is arranged on the blood return line 9.

The blood reservoir 11 has an inlet 13 to which a first section 9A of the blood return line 9 runs, and has an outlet 14 from which a second section 9B of the blood return line 9 leads away. To detect a given filled level in the blood reservoir 11, the dialysis apparatus may have a filled-level sensor 15 which detects when the filled level in the container reaches a preset value. As well as this, what is also provided is a pressure sensor 16 which measures the pressure in the blood reservoir 11.

When the blood reservoir 11 is filled with blood, a certain volume of air is left in the blood reservoir above the level 17 of the liquid. The blood reservoir 11 is in flow-permitting connection with a device 18 for storing gas, and in particular air, which takes the form of a container containing a sealed-off volume of space. The device 18 for storing gas will be referred to in what follows as an air reservoir.

To enable the blood reservoir 11 and air reservoir 18 to communicate with one another, a line 19 which runs to the air reservoir 18 leads away from the top of the blood reservoir 11. Arranged in the line 19 is a device 20 for compressing gas which may for example take the form of a conventional compressor. As long as the compressor is not being operated, the said compressor breaks the flow-permitting connection between the blood reservoir and the air reservoir. When on the other hand the compressor is operating, air present in the air reservoir is transferred to the blood reservoir. Because the air is compressed a preset pressure builds up in the blood reservoir.

The line 19 has two sections 19A, 19B, of which one section 19A connects the blood reservoir 11 to the discharge-end connection 20A of the compressor 20 and of which the other section 19B connects the inlet-end connection 20B of the compressor 20 to the air reservoir 18. These sections 19A, 19B of the line form a connecting path for the transfer of gas from the air reservoir to the blood reservoir.

Provided to enable air to be transferred from the blood reservoir 11 to the air reservoir 18 when the compressor 20 is not operating is a bypass line 21 which leads away from the first section 19A of the line 19 and runs to the second section 19B of the line 19. Connected into the bypass line 21 is a bypass valve 22. Together with the corresponding sections of the line 19, the bypass line 21 forms a connecting path for feeding gas from the blood reservoir to the air reservoir.

To prevent liquid from being able to make its way from the blood reservoir 11 to the air reservoir 18, there is arranged in the first section 19A of the line 19 a filter 23 which contains a membrane which is hydrophobic, i.e., which is permeable to air but impermeable to liquid. However, because the filling of the blood reservoir takes place only to a maximum filled level, liquid can in any case only makes its way into the line 19 in the event of a fault.

For air to be admitted to/released from the sealed-off volume of space which comprises the blood reservoir 11 and the air reservoir 18 plus the line 19 and line 21, a device 24 for air admission/release is provided which has an air admission/release line 24A, having an air admission/release valve 24B, which is connected for example to the first section 19A of the line 19. Basically, the air admission/release line 24A can lead away from any point on the volume of space which air is to be admitted to/released from. The admission/release of air should take place in particular in the apparatus-side part of the system as a whole.

In addition to the pressure sensor 16 for measuring the pressure in the blood reservoir 11, what are also provided are a pressure sensor 25 for measuring the pressure in the first section 19A of the line 19 between the filter 23 and the compressor 20, and a further pressure sensor 26 for measuring the pressure in the air reservoir 18.

The pressure sensors 16, 25 and 26 are pressure sensors for measuring relative pressures in the present exemplary embodiment. There is a further pressure sensor 31 provided to measure ambient pressure.

As well as this, what are also provided are a temperature sensor 28 for measuring the temperature of the air present in the air reservoir 18, a temperature sensor 29 for measuring the temperature of the air present in the blood reservoir 11, and a temperature sensor 30 to measure the temperature of the air present in the first section 19A of the line 19.

The dialysis apparatus has a central control and calculating unit 27 which has electrical lines (not shown) to the blood pump 6, the venous tube clamp 12, the bypass valve 22, the air admission/release valve 24B, the compressor 20 and to the temperature sensors 28, 29, 30, and also to the pressure sensors 16, 25, 26 for measuring relative pressures and to the pressure sensor 31 for measuring ambient pressure. The central control and calculating unit 27 is connected in turn to an input unit (not shown) which forms an interface between the user and the machine.

The control and calculating unit 27 calculates the values of the absolute pressures from the values of the relative pressures which are measured by the pressure sensors 16, 25 and 26 and from the ambient pressure which is measured by the pressure sensor 31.

In what follows, the operation of the dialysis apparatus will be described in detail by reference to FIGS. 2 and 3. The central control and calculating unit 27 controls the dialysis machine as follows.

Figure 2:
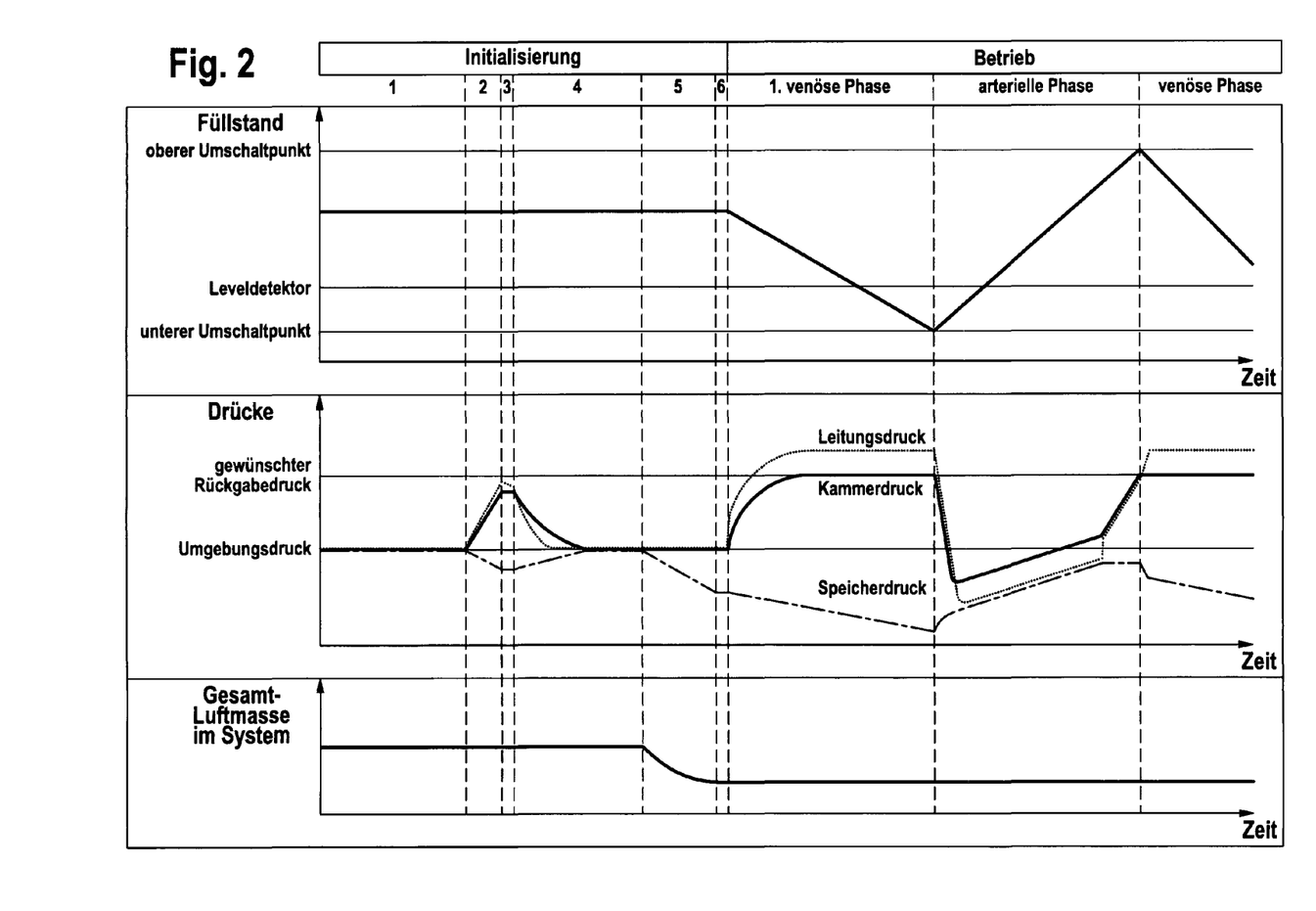
FIG. 2 shows the curves followed by filled level and pressure during the initialisation and operation of the blood-treatment apparatus according to the present invention.

FIG. 2 shows the filled level in the blood reservoir 11 as a function of time during the individual phases 1 to 6 of the initialisation. As well as this, FIG. 2 also shows the curves which are followed, in the individual phases 1 to 6 of the initialisation, by the pressure in the blood reservoir 11, which will be referred to as the blood reservoir pressure $p_{Blood\ reservoir}$, by the pressure in the air reservoir 18, which will be referred to as the air reservoir pressure $p_{Air\ reservoir}$, and by the pressure in the first section 19A of the line 19, which will be referred to as the line pressure $p_{Line}$. FIG. 2 also shows the curve followed over time, in the individual phases 1 to 6 of the initialisation, by the total mass of air enclosed in the blood reservoir 11 and in the air reservoir 18 and the relevant sections of the lines 19, 22.

The initialisation according to the present invention of the system is performed, by the method steps which are described below, at the beginning of the dialysis treatment proper. Basically, the initialisation can take place at any time during the operation of the blood-treatment apparatus, it not being necessary for any given level of blood to be present in the blood reservoir.

Regardless of whether or not the initialisation concerned is the first during the blood treatment, at the beginning of the initialisation the bypass valve 22 and the air admission/release valve 24B are opened by the control and calculating unit 27 to bring both the blood reservoir pressure $p_{Blood\ reservoir}$ in the blood reservoir 11 and the air reservoir pressure $p_{Air\ reservoir}$ in the air reservoir 18 to ambient pressure.

Then, in a memory (not shown) of the control and calculating unit 27, the blood reservoir pressure $p_{Blood\ reservoir}$ which arises itself in the blood reservoir at the time $t_0$ following the admission/release of air, and the air reservoir pressure $p_{Air\ reservoir}$ which arises in the air reservoir 18 at this time are determined for the purposes of the calculation at a later point in time of the pressure to be set in the blood reservoir 11. The relative blood reservoir pressure $p_{Blood\ reservoir}$ can be measured by the pressure sensor 16 or the pressure sensor 25 because it can be assumed that the same pressure, i.e., ambient pressure, has arisen both in the blood reservoir 11 and in the line 19 which is connected to the blood reservoir. The relative air reservoir pressure $p_{Air\ reservoir}$ is measured by the pressure sensor 26. From the values of relative pressure and from the ambient pressure which is measured, the control and calculating unit 27 calculates the absolutes values for the blood reservoir pressure $p_{Blood\ reservoir}$ and air reservoir pressure $p_{Air\ reservoir}$. However, to simplify, it is also possible for the blood reservoir pressure $p_{Blood\ reservoir}$ in the blood reservoir 11 and the air reservoir pressure $p_{Air\ reservoir}$ in the air reservoir 18 to be assumed to be, at time $t_0$, the ambient pressure which is measured (step 1).

Following this, the bypass valve 22 and the air admission/release valve 24B are closed by the control and calculating unit 27 and the compressor 20 is operated until such time as the blood reservoir pressure $p_{Blood\ reservoir}$ reaches a preset value (step 2).

Then, after an equalisation of the blood reservoir pressure $p_{Blood\ reservoir}$ and the line pressure $p_{Line}$ in the line 19, the blood reservoir pressure $p_{Blood\ reservoir}$ in the blood reservoir 11 (i.e., the line pressure $p_{Line}$ in the line 19) and the air reservoir pressure $p_{Air\ reservoir}$ in the air reservoir 18 are determined at time $t_1$.

Following the measurement of pressure, the volume of air, and hence the level of liquid, in the blood reservoir 11 is determined (step 3). The volume of air $V_{Blood\ reservoir\ air}$ in the blood reservoir 11 is calculated by the control and calculating unit 27 from the following equation (1):

$$V_{Blood\ reservoir\ air} = -\frac{(p_{Air\ reservoir\_t0} - p_{Air\ reservoir\_t1})}{(p_{Blood\ reservoir\_t0} - p_{Blood\ reservoir\_t1})} \cdot V_{Air\ reservoir} - V_{Line} \qquad \text{Equation (1)}$$

$V_{Blood\ reservoir\ air}$: Calculated volume of air in the blood reservoir $V_{Air\ reservoir}$: Known volume of the air reservoir $V_{Line}$: Known volume of the line $p_{Air\ reservoir\_t0}$: Air reservoir pressure before the shift in volume, at time $t_0$ $p_{Air\ reservoir\_t1}$: Air reservoir pressure after the shift in volume, at time $t_1$ $p_{Blood\ reservoir\_t0}$: Blood reservoir pressure before the shift in volume, at time $t_0$ $p_{Blood\ reservoir\_t1}$: Blood reservoir pressure after the shift in volume, at time t1

Once the volume of air $V_{Blood\ reservoir\ air}$ in the blood reservoir 11 is known, the control and calculating unit 27 calculates the maximum permitted pressure $p_{Air\ reservoir\ max}$ in the air reservoir 18 for the volume of air in the blood reservoir which has been determined, from the following equation (2). The maximum permitted pressure $p_{Air\ reservoir\ max.}$ which is set in the air reservoir 18 is intended not to produce a pressure above atmospheric in the blood reservoir 11 when the upper changeover point is approached in the said blood reservoir.

$$p_{Air\ reservoir\ max.} = \qquad \text{Equation (2)}$$

$$(\hat{m}_{Max.\ total} - \hat{m}_{Line} - \hat{m}_{Blood\ reservoir}) \cdot \frac{T_{Air\ reservoir}}{V_{Air\ reservoir}}$$

$$\hat{m}_{Max.\ total} = \left( \frac{V_{Air\ reservoir}}{T_{Air\ reservoir}} + \frac{V_{Line}}{T_{Line}} + \frac{V_{Blood\ reservoir} - V_{Max.\ UT}}{T_{Blood\ reservoir}} \right) \cdot p_{Abs}$$

$$\hat{m}_{Line} = \frac{p_{Abs} \cdot V_{Line}}{T_{Line}}$$

$$\hat{m}_{Blood\ reservoir} = \frac{p_{Abs} \cdot V_{Blood\ reservoir\ air}}{T_{Blood\ reservoir}}$$

$p_{Air\ reservoir\ max.}$: Pressure in the air reservoir (air reservoir pressure) to be set $V_{Max.\ UT}$: Volume in the blood reservoir at the maximum blood level in operation The values for the temperatures $T_{Blood\ reservoir}$ in the blood reservoir, $T_{Air\ reservoir}$ in the air reservoir and $T_{Line}$ in the line which are required for calculating the maximum permitted pressure $p_{Air\ reservoir\ max.}$ in the air reservoir are received by the control and calculating unit 27 from the relevant temperature sensors 28, 29 and 30.

To simplify calculation in the case of the gas equations, the humidity of the air is ignored in the present exemplary embodiment. Nor is any account taken of the parameters of the compressor 20. If even more accurate values are to be determined for the maximum permitted air reservoir pressure $p_{Air\ reservoir\ max.}$, the humidity of the air and/or the parameters of the compressor may also be taken into account. Appropriate sensors for the humidity of the air have to be provided for this purpose.

The bypass valve 22 and the air admission/release valve 24B are now opened to bring both the blood reservoir pressure $p_{Blood\ reservoir}$ and the air reservoir pressure $p_{Air\ reservoir}$ to ambient pressure (step 4). A defined starting state is thus established for the subsequent adjustment of the mass of air in the system. The bypass valve 22 is then closed, with the air admission/release valve 24B remaining open, and the compressor 20 is operated until such time as an air reservoir pressure $p_{Air\ reservoir\ max.}$ has arisen in the air reservoir 18, as a result of which a pressure above atmospheric does not arise in the blood reservoir in the subsequent course of treatment when the upper changeover point is approached (step 5). In the process, the compressor 20 feeds air into the surroundings via the air admission/release valve 24B to reduce the mass of air in the system.

The calculation of the maximum permitted air reservoir pressure $p_{Air\ reservoir\ max.}$ will again be explained by reference to the present exemplary embodiment by taking some actual numerical values.

Ambient pressure: 750 mmHg

Current filled level in the blood reservoir: 35 ml

Maximum blood level in the blood reservoir: 50 ml.

Determination of the volume of air in the blood reservoir from equation 1:

$$V_{Blood\ reservoir\ air} = \frac{(750\ \text{mmHg} - 700\ \text{mmHg})}{(750\ \text{mmHg} - 1083\ \text{mmHg})} \cdot 308\ \text{ml} - 7\ \text{ml} = 45\ \text{ml}$$

Determination of the pressure to be set in the device for storing gas from equation 2:

$$p_{Air\ reservoir\ max.} =$$

$$(\hat{m}_{Max.\ total} - \hat{m}_{Line} - \hat{m}_{Blood\ reservoir}) \cdot \frac{309\text{K}}{308\ \text{ml}} = 699\ \text{mmHg}$$

where the auxiliary variables $\hat{m}_{Max,\ total}$, $\hat{m}_{Line}$, $\hat{m}_{Blood\ reservoir}$ and for the masses are:

$$\hat{m}_{Max.\ total} = \left( \frac{308\ \text{ml}}{309\text{K}} + \frac{7\ \text{ml}}{309\text{K}} + \frac{80\ \text{ml} - 50\ \text{ml}}{309\text{K}} \right) \cdot 750\ \text{mmHg}$$

$$\hat{m}_{Line} = \frac{750\ \text{mmHg} \cdot 7\ \text{ml}}{309\text{K}}$$

$$\hat{m}_{Blood\ reservoir} = \frac{750\ \text{mmHg} \cdot 45\ \text{ml}}{309\text{K}}$$

A pressure (below atmospheric) of 699 mmHg is set in the air reservoir 18 by means of the compressor 20. This ensures that, after the initialisation, during the arterial and venous phases, a pressure above the ambient pressure of 750 mmHG, which might result in a hazard to the patient, does not arise in the blood reservoir 11 when the blood level in the blood reservoir is at a maximum.

As the final step, the mass of air contained in the system is calculated (step 6). This will be explained in detail at a later stage. The air admission/release valve 24B remains closed during the whole of the blood treatment unless a fresh initialisation, following the detection of an air leak for example, is required. The initialisation thus comes to an end and the blood treatment starts with the first venous phase or the venous phase, as the case may be.

Once the air admission/release valve has closed, the mass of air in the system remains constant. The compressor 20 can be used to set various operating points by means of displacements of masses of air. However, the sum of the masses of air must always correspond to the mass of air at the time of the air admission/release. If this is not the case, then there is a fault in one or more of the pressure sensors. From the errors which occur at the different operating points it is possible, by mathematical and statistical methods, to draw conclusions as to the faults in the individual sensors, thus making it possible for the fault to be corrected. The analysis of the individual sensors for faults by an analysis of the masses of air at the different operating points is possible, independently of the prescribed initialisation, either before the initialisation (the normal case) or after the initialisation or even during the treatment.

The initialisation of the system as described above is followed by the venous and arterial phases.

In the first venous phase, the compressor 20 is operated with the bypass valve 22 closed, the venous tube clamp 12 being open and the blood pump 6 being stopped. As the compressor operates, air from the air reservoir 18 is compressed and is fed to the blood reservoir 11. As a result, the blood reservoir pressure and the line pressure rise whereas the air reservoir pressure falls. At the same time, there is a continuous drop in the filled level in the blood reservoir until the level of the lower changeover point is reached. In the course of this, it is crucial for the air reservoir pressure to be below the blood reservoir pressure, and thus below the line pressure too, to prevent any gas from entering the blood reservoir from the air reservoir if there should happen to be a fault. What is aimed for in addition is for the blood reservoir pressure even to be below ambient pressure.

The arterial phase, in which the blood reservoir is again filled with blood withdrawn from the patient, thereupon begins, and this is again followed by the venous phase, in which the blood from the blood reservoir is again fed to the patient.

The air reservoir is sized to be sufficiently large for enough air to be present in the system, even at the end of the venous phase, for the desired return pressure to be able to be maintained in the blood reservoir. To enable all operating points to be set with the same initialisation with a return pressure of 0 to 500 mmHg relative for a cardiac output of up to 60 ml, what is required in practice is an air reservoir with a volume of approx. 300 ml.

Figure 3:
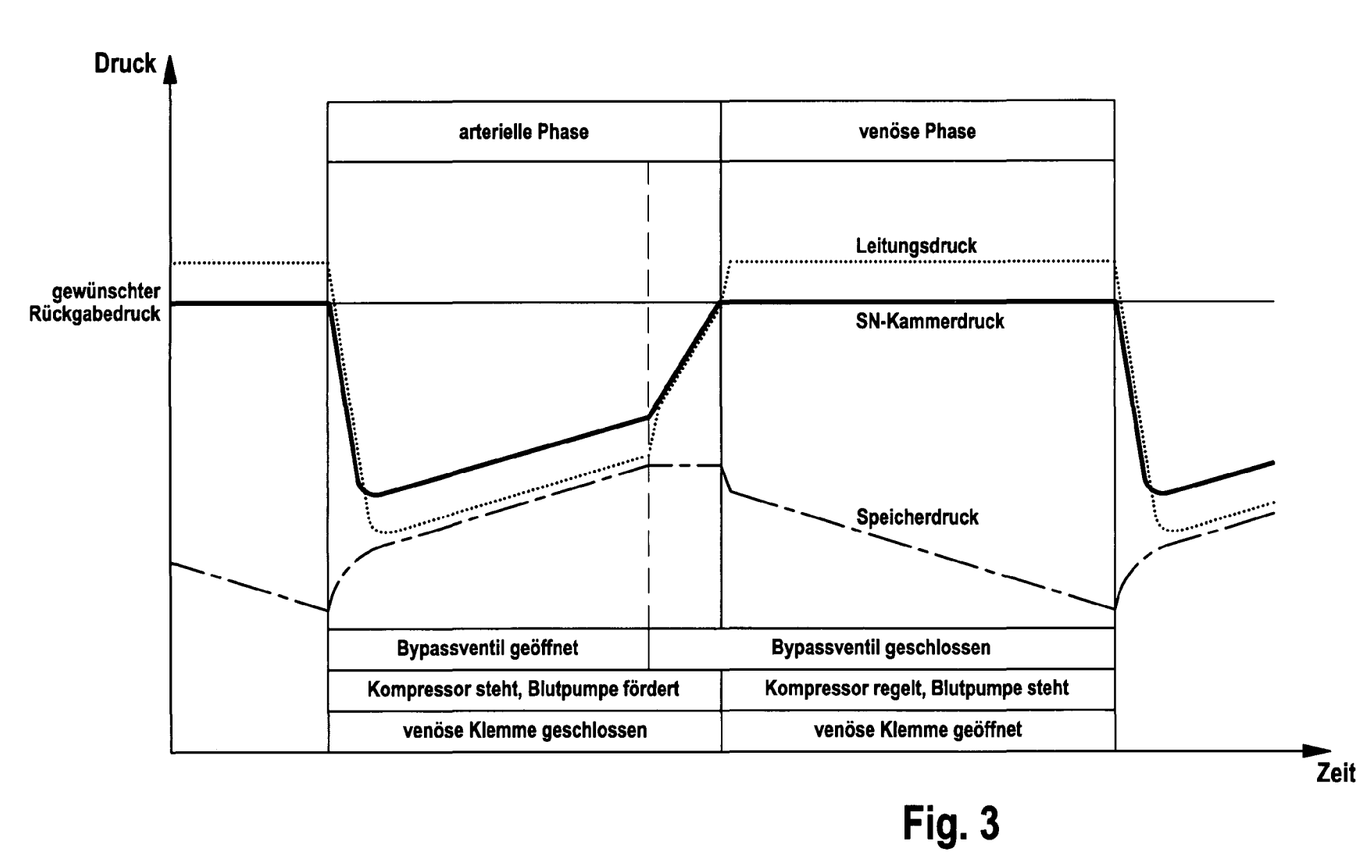
FIG. 3 shows the curves followed by pressure during the successive arterial and venous phases.

The curves followed over time by the blood reservoir pressure and air reservoir pressure and by the line pressure during the arterial and venous phases proper after the initialisation of the system are shown in FIG. 3, which shows a detail of FIG. 2.

The blood pump 6 is operated, with the compressor 20 stopped, during the whole of the arterial phase. The venous tube clamp 12 remains closed during the whole of the arterial phase.

At the beginning of the arterial phase, the control and calculating unit 27 opens the bypass valve 22, and the air which is expelled from the blood reservoir 11 thus makes its way via the bypass line 21 into the air reservoir 18. Consequently the pressure in the air reservoir rises whereas the pressure in the blood reservoir and the line pressure initially fall before then likewise rising virtually with the pressure in the air reservoir. There is a thus a continuous fall in the mass of air contained in the blood reservoir and in the associated volume of space in the line.

As soon as the mass of air contained in the blood reservoir and in the volume of space in the line is of a preset size which is given by the desired cardiac output and the desired return pressure, the control and calculating unit closes the bypass valve. Consequently, there are two separate volumes of air which come into being, i.e., the volume of air in the blood reservoir and in the associated sections of line and the volume in the air reservoir and in the associated sections of line. The blood pump is then operated, with the bypass valve closed, and the air reservoir pressure thus remains constant whereas the air in the blood reservoir and in the associated volume of space in the line is compressed until such time as, when the desired cardiac output is reached, the desired return pressure is reached too. FIG. 3 shows that at the end of the arterial phase the blood reservoir and line pressure has risen to the desired return pressure, with the air reservoir pressure always being below the blood reservoir and line pressure, and in particular below ambient pressure, during the whole of the arterial phase. This rules out the possibility of air making its way out of the air reservoir and into the blood reservoir even if there is a fault in the system, such for example as a leak in the compressor.

Rather than the arterial phase being divided into a first and a second interval of time, there are also other possible exemplary embodiments with which the advantages according to the present invention can equally well be achieved. One alternative exemplary embodiment makes provision for use to be made, instead of the bypass valve 22, of a valve which is controlled in response to pressure by means of the control unit and which opens when a limiting pressure corresponding to the return pressure is reached, so that a constant pressure prevails in the blood reservoir for a certain length of time.

The control and calculating unit then changes over to the venous phase, with the bypass valve remaining open, the blood pump being stopped and the compressor started, and the venous tube clamp being opened. The compressor is operated during the whole of the venous phase, with the blood pump stopped. The venous tube clamp remains open and the bypass valve closed during the venous phase.

The compressor feeds air out of the air reservoir and into the blood reservoir to generate a pressure above atmospheric and blood is thus fed out of the blood reservoir. The compressor is so operated in this case that the desired return pressure arises in the blood reservoir. Because air is fed continuously to the blood reservoir from the air reservoir, there is a continuous fall in the pressure in the air reservoir. What is crucial is, once again, that the pressure in the air reservoir is always below the pressure in the blood reservoir and the line, and is preferably also below ambient pressure, thus ruling out any possibility of an infusion of air from the air reservoir into the patient in the event of a fault. The venous phase then comes to an end when the blood level in the blood reservoir has again fallen to the level equivalent to the lower changeover point. The next arterial phase then follows.

The calculation of the volume of blood $V_{Blood}$ present in the blood reservoir, which calculation is performed continuously or at preset intervals by the control and calculating unit while the dialysis apparatus is operating, will be described in what follows. If this volume of blood is known, this knowledge can be used to make a comparison with the changeover point from the arterial to the venous phase or vice versa.

For the volume of blood $V_{Blood}$ present in the blood reservoir to be calculated, it is first necessary for the mass of air in the blood reservoir to be determined. Once the equalisation of pressure has taken place, what is true is:

$$pV = \frac{m}{M_m} RT$$

where:
p=pressure (absolute), V=volume, m=mass, $M_m$=molar mass, R=general gas constant and T=temperature.

Because $M_m$ and R are known and constant and the absolute sizes of the masses of air as such are not required, it is enough in practice for the calculation to be carried out with auxiliary variables for the masses which are proportional to mass but whose unit is not that of a mass. Hence it is only the following auxiliary variables which have to be determined.

$$\hat{m} = pV/T$$

where $$\hat{m} \neq m$$

To determine the auxiliary variable for the total mass of air, the sum of all the auxiliary variables for the part masses of air, i.e., for the masses of air in the blood reservoir, in the associated lines and in the air reservoir, has to be found. For this purpose, all the volumes of space which are filled with air have to be multiplied by the respective pressures prevailing therein and divided by the temperature.

$$\left(\frac{pV}{T}\right)_{Tot.} =$$

$$\frac{p_{Blood\ reservoir} \cdot V_{Blood\ reservoir}}{T_{Blood\ reservoir}} + \frac{p_{Line} \cdot V_{Line}}{T_{Line}} + \frac{p_{Air\ reservoir} \cdot V_{Air\ reservoir}}{T_{Air\ reservoir}}$$

$$T_{Blood\ reservoir} \approx 273.15K + 36K$$

$$T_{Line} \approx \frac{T_{Blood\ reservoir} | T_{Air\ reservoir}}{2}$$

The volume of air in the blood reservoir $V_{Blood\ reservoir\ air}$ varies during operation. When the blood level is at the height H corresponding to the level detected by the filled-level detector 15, then $$V_{Blood\ reservoir\ air} = V_{Blood\ reservoir\ air/LT} - \Delta V_{Blood\ reservoir/LT-H}$$

where $V_{Blood\ reservoir\ air/LT}$ is the volume of air in the blood reservoir at the lower changeover point LT and $\Delta V_{Blood\ reservoir/LT-H}$ is the difference in volume between the lower changeover point LT and the height H corresponding to the level detected by the filled-level detector 15 in the blood reservoir.

At the end of the initialisation, there is in addition, at the upper changeover point UT, blood of the total cardiac output volume $V_{Output}$ in the blood reservoir, which means that $$V_{Blood\ reservoir\ air} = V_{Blood\ reservoir\ air/LT} - \Delta V_{Output}.$$

The rest of the volumes remain constant. The temperatures can be assumed to be constant in this case to a good approximation if no correction is made for temperature. However, a temperature sensor for measuring temperature is preferably provided at least in the air reservoir, thus enabling a connection to be made for temperature. Temperature sensors may however also be provided for the other values of pressure.

The volume of blood $V_{Blood}$ in the blood reservoir which is fed is calculated during the entire cycle in each repeat of the program. When this is done, the volume of air $V_{Blood\ reservoir\ air}$ enclosed in the blood reservoir is calculated from the pressures measured and the difference between the volume of air in the blood reservoir at the lower changeover point LT and the full volume of air in the blood reservoir is found.

$$V_{Blood\ reservoir\ air} = \frac{\left(\frac{pV}{T}\right)_{Total} - \frac{p_{Line}V_{Line}}{T_{Line}} - \frac{p_{Air\ reservoir}V_{Air\ reservoir}}{T_{Air\ reservoir}}}{\frac{p_{Blood\ reservoir}}{T_{Blood\ reservoir}}}$$

$$V_{Blood} = V_{Blood\ reservoir\ air/LT} - \Delta V_{Blood\ reservoir\ air}$$

The auxiliary variable for the total mass of air $$\hat{m}_{Total} = \left(\frac{pV}{T}\right)_{Total}$$

and the total mass $m_{Total}$ remain unchanged after the initialisation of the system because the air release valve remains closed. Because the calculation of the volume of blood $V_{Blood}$ is performed with the blood pump running or the compressor running, smoothing is performed of the pressure signals and of the volume of blood $V_{Blood}$ which is calculated.

The changeover from the arterial to the venous phase (UT) takes place when the difference between the volume of blood calculated $V_{Blood}$ and the cardiac output $V_{Output}$ which is set is zero, and the changeover from the venous to the arterial phase takes place when the volume of blood calculated is zero.

In what follows, it will be described how the control and calculating unit calculates the point in time at which a changeover is made, within the arterial phase, between the first and second intervals of time making up the arterial phase.

As has already been described above, it is possible for the changeover point from the arterial phase to the venous phase and back to be found simply by comparing the volume of blood with the cardiac output or with zero. As already mentioned, the arterial phase is divided into a first and a second interval of time. In the first arterial phase the blood pump pumps blood, with the bypass valve open, via the dialyser into the blood reservoir. The pressure below atmospheric which had previously built up in the air reservoir during the venous phase is thus used to assist the pump. In the second arterial phase, the air reservoir is uncoupled from the rest of the system by closing the bypass valve and there is a sharp rise in the pressure in the blood reservoir due to the volume of blood which is fed. At the end of the second arterial phase the requisite desired pressure needs to be present in the blood reservoir. The changeover point between the first and second arterial phases must therefore be selected in such a way that the volume of blood with is still outstanding generates the desired pressure in the blood reservoir and the line by the time of the upper changeover point UT.

What therefore has to be calculated is the mass of air which, when compressed, at the upper changeover point UT, to the volume available in the blood reservoir and the line, will generate the desired pressure $p_{Desired}$. The mass of air in the blood reservoir and the line is $$\frac{p_{Blood\ reservoir}V_{Blood\ reservoir}}{T_{Blood\ reservoir}} + \frac{p_{Line}V_{Line}}{T_{Line}} =$$

$$\left(\frac{pV}{T}\right)_{Tot.} - \frac{p_{Air\ reservoir}V_{Air\ reservoir}}{T_{Air\ reservoir}}$$

At the changeover point from the first to the second of the intervals of time making up the arterial phase, the mass of the air in the blood reservoir and the line must be equal to the mass of the air which is present in the blood reservoir and the line at the upper changeover point UT.

$$\left(\frac{pV}{T}\right)_{Tot.} =$$

$$\frac{p_{Air\ reservoir}V_{Air\ reservoir}}{T_{Air\ reservoir}} = \frac{p_{Desired} \cdot V_{Blood\ reservoir\ air/UT}}{T_{Blood\ reservoir}} + \frac{p_{desired} \cdot V_{Line}}{T_{Line}}$$

where $V_{Blood\ reservoir\ air/UT}$ is the volume of air in the blood reservoir at the upper changeover point UT.

The invention claimed is:

1. A method of using a blood-treatment apparatus for single-needle mode, comprising:

during an arterial phase, making a connection between a device for amassing blood which encloses a sealed-off volume of space, and a device for storing gas which encloses a sealed-off volume of space, the device for amassing blood and the device for storing gas forming, together with a device for making a connection between the device for amassing blood and the device for storing gas, a sealed volume, which no gas can enter and from which no gas can exit, and feeding blood to the device for amassing blood, gas which is expelled from the sealed-off volume of space in the device for amassing blood being transferred to the device for storing gas, thus causing a pressure to be generated in the device for storing gas; and during a venous phase, making a connection between the device for storing gas and the device for amassing blood, the device for amassing blood and the device for storing gas forming, together with the device for making a connection between the device for amassing blood and the device for storing gas, a sealed volume, which no gas can enter and from which no gas can exit, and gas which has been stored in the device for storing gas is transferred to the device for amassing blood, thus expelling the blood which is contained in the sealed-off volume of space in the device for amassing blood, an ongoing changeover being made between the arterial phase in which the device for amassing blood is filled with blood to an upper changeover point and the venous phase in which the device for amassing blood is emptied to a lower changeover point, thus causing blood to be fed to the extra-corporeal blood circuit in the arterial phase and blood to be extracted from the extra-corporeal blood circuit in the venous phase;

wherein, for initialisation of successive arterial and venous phases, a pressure $p_{Air\ reservoir\ max.}$ which is to be set in the device for storing gas is calculated and, for the initialisation, the pressure $p_{Air\ reservoir\ max.}$ previously calculated is set in the device for storing gas before the arterial and venous phases are started.

2. The method according to claim 1, wherein, to set the pressure $p_{Air\ reservoir\ max.}$ which is to be set in the device for storing gas, gas is discharged from the device for storing gas or gas is fed to the device for storing gas.

3. The method according to claim 1, wherein, to calculate the pressure $p_{Air\ reservoir\ max.}$ which is to be set in the device for storing gas, a volume of gas contained in the device for amassing blood is determined and the pressure $p_{Air\ reservoir\ max.}$ which is to be set in the device for storing gas is determined based on the volume of gas contained in the device for amassing blood.

4. The method according to claim 3, wherein, to determine the volume of gas contained in the device for amassing blood, gas is transferred from the device for storing gas to the device for amassing blood to produce a preset difference in pressure between the device for storing gas and the device for amassing blood, an absolute pressure in the device for storing gas and an absolute pressure in the device for amassing blood being determined before and after production of the difference in pressure.

5. The method according to claim 4, wherein, to determine the absolute pressure, ambient pressure is measured, and respective relative pressures are measured in the device for storing gas and the device for amassing blood, values of the absolute pressure being calculated from values of the relative pressures and of ambient pressure.

6. The method according to claim 4, wherein, before gas is transferred from the device for storing gas to the device for amassing blood, a pressure which corresponds to ambient pressure is set in the sealed-off volume of space in the device for amassing blood and in the sealed-off volume of space in the device for storing gas.

7. The method according to claim 6, wherein, to set the ambient pressure, a connection is made between the device for storing gas and the device for amassing blood and air is admitted to/released from the device for storing gas and/or the device for amassing blood.

8. An apparatus for blood treatment for single-needle mode, comprising:

a device for amassing blood which encloses a sealed-off volume of space;

a device for storing gas which encloses a sealed-off volume of space;

a device for making a connection between the device for amassing blood and the device for storing gas, wherein the device for amassing blood and the device for storing gas form, together with the device for making a connection between the device for amassing blood and the device for storing gas, a sealed volume, which no gas can enter and from which no gas can exit;

a device for feeding blood to the device for amassing blood in an extra-corporeal blood circuit, the extra-corporeal blood circuit having a blood infeed line which runs to an inlet of a blood-treating unit and a blood return line which leads away from an outlet of the blood-treating unit;

a device for compressing gas; and a control and calculating unit which co-operates with the device for amassing blood, with the device for storing gas, with the device for making a connection between the device for amassing blood and the device for storing gas and with the device for compressing gas such that, in an arterial phase when the device for amassing blood is being filled, gas which is expelled from the device for amassing blood is transferred to the device for storing gas and, in a venous phase for emptying the device for amassing blood, gas which has been stored in the device for storing gas is transferred to the device for amassing blood by the device for compressing gas, blood thus being able to be transferred to the extra-corporeal blood circuit in the arterial phase and to be extracted from the extra-corporeal blood circuit in the venous phase, wherein the control and calculating unit is configured such that, for initialisation of successive arterial and venous phases, a pressure $p_{Air\ reservoir\ max.}$ which is to be set in the device for storing gas is calculated and, for the initialisation, the pressure $p_{Air\ reservoir\ max.}$ previously calculated is set in the device for storing gas before the arterial and venous phases are started and, on the pressure being set, the arterial and venous phases are started.

9. The apparatus according to claim 8, wherein the control and calculating unit is configured such that, to set the pressure $p_{Air\ reservoir\ max.}$ which is to be set in the device for storing gas, the device for compressing gas is operated, thus causing gas to be discharged from the device for storing gas or gas to be fed to the device for storing gas.

10. The apparatus according to claim 8, wherein the control and calculating unit is configured such that, to calculate the pressure $p_{Air\ reservoir\ max.}$ which is to be set in the device for storing gas, a volume of gas contained in the device for amassing blood is determined and the pressure $p_{Air\ reservoir\ max.}$ which is to be set in the device for storing gas is determined based on the volume of gas contained in the device for amassing blood.

11. The apparatus according to claim 10, wherein a device for determining absolute pressure is provided in the device for amassing blood and the device for storing gas, the control and calculating unit being configured such that, to determine the volume of gas contained in the device for amassing blood, gas is transferred from the device for storing gas to the device for amassing blood to produce a preset difference in pressure between the device for amassing blood and the device for storing gas, and the absolute pressure in the device for storing gas and the absolute pressure in the device for amassing blood are determined before and after production of the difference in pressure.

12. The apparatus according to claim 11, wherein the device for determining absolute pressure includes a device for measuring ambient pressure, a device for measuring relative pressure in the device for storing gas, and a device for measuring relative pressure in the device for amassing blood, the control and calculating unit being configured such that respective values of absolute pressure are calculated from measured values of relative pressure and ambient pressure.

13. The apparatus according to claim 8, wherein the device for making a connection between the device for amassing blood and the device for storing gas has a first connecting path and a second connecting path, the first connecting path having a bypass line, having a bypass valve, which connects the device for amassing blood to the device for storing gas, and the second connecting path having a line for feeding gas, the device for compressing gas being arranged in the line for feeding gas.

14. The apparatus according to claim 11, wherein the control and calculating unit is configured such that, before gas is transferred from the device for storing gas to the device for amassing blood, a pressure which corresponds to ambient pressure is set to produce a difference in pressure in the sealed-off volume of space in the device for amassing blood and in the sealed-off volume of space in the device for storing gas.

15. The apparatus according to claim 14, wherein a device for air admission/release is provided, the control and calculating unit being configured such that, to set the ambient pressure, a connection is made between the device for storing gas and the device for amassing blood, and air is admitted to/released from the device for storing gas and/or the device for amassing blood.

16. The apparatus according to claim 13, wherein the line for feeding gas has a first section which connects the device for amassing blood to the discharge end of the device for compressing gas, and a second section which connects the inlet end of the device for compressing gas to the device for storing gas, the device for air admission/release being provided in the first section of the line.

17. The apparatus according to claim 8, wherein the device for amassing blood takes the form of a container of a preset volume which is arranged in the blood return line of the extra-corporeal blood circuit.

18. The apparatus according to claim 8, wherein the device for storing gas takes the form of a container of a preset volume.

19. The apparatus according to claim 8, wherein the device for feeding blood in the extra-corporeal blood circuit takes the form of a blood pump which is arranged in the blood infeed line.

20. The apparatus according to claim 8, wherein the control and calculating unit has a device for changing over between the arterial phase and the venous phase which are configured such that the device for feeding blood in the extra-corporeal blood circuit is operated in the arterial phase, the device for amassing blood being connected to the device for storing gas, thus causing gas expelled from the device for amassing blood to be transferred to the device for storing gas when the device for amassing blood is being filled, and the device for compressing gas is operated in the venous phase, the device for storing gas being connected to the device for amassing blood, thus causing gas which has been stored in the device for storing gas to be transferred to the device for amassing blood by the device for compressing gas to empty the device for amassing blood.

* * * * *